United States Patent
Frauenkron et al.

(10) Patent No.: US 7,601,875 B2
(45) Date of Patent: Oct. 13, 2009

(54) METHOD FOR PRODUCING ETHYLENEAMINES

(75) Inventors: Matthias Frauenkron, Freinsheim (DE); Holger Evers, Mannheim (DE); Johann-Peter Melder, Böhl-Iggelheim (DE); Roderich Röttger, Mannheim (DE); Markus Siegert, Heidelberg (DE); Till Gerlack, Ludwigshafen (DE); Jan Nouwen, Brecht (BE); Thomas Krug, Worms (DE)

(73) Assignee: BASF Aktiengesellschaft (DE)

( * ) Notice: Subject to any disclaimer, the term of this patent is extended or adjusted under 35 U.S.C. 154(b) by 613 days.

(21) Appl. No.: 10/566,694

(22) PCT Filed: Jul. 8, 2004

(86) PCT No.: PCT/EP2004/007471

§ 371 (c)(1),
(2), (4) Date: Feb. 20, 2006

(87) PCT Pub. No.: WO2005/014523

PCT Pub. Date: Feb. 17, 2005

(65) Prior Publication Data

US 2007/0100144 A1 May 3, 2007

(30) Foreign Application Priority Data

Aug. 1, 2003 (DE) ................. 103 35 991

(51) Int. Cl.
C07C 209/16 (2006.01)
(52) U.S. Cl. ....................... 564/479; 564/480
(58) Field of Classification Search ........... None
See application file for complete search history.

(56) References Cited

U.S. PATENT DOCUMENTS

| 2,861,995 | A | 11/1958 | MacKenzie |
| 3,714,259 | A | 1/1973 | Lichtenwalter et al. |
| 3,766,184 | A | 10/1973 | Johansson et al. |
| 4,014,933 | A | 3/1977 | Boettger et al. |
| 4,234,730 | A | 11/1980 | McConnell et al. |
| 4,568,746 | A | 2/1986 | Cowherd, III |
| 4,609,761 | A | 9/1986 | Watts, Jr. et al. |
| 4,612,397 | A | 9/1986 | Renken |
| 4,647,701 | A | 3/1987 | Gibson |
| 4,683,335 | A | 7/1987 | Knifton et al. |
| 5,410,086 | A | 4/1995 | Burgess |

FOREIGN PATENT DOCUMENTS

| DE | 1170960 | 5/1964 |
| DE | 158393 | 1/1983 |
| DE | 213 206 | 9/1984 |
| DE | 217 507 | 1/1985 |
| EP | 0 197 611 | 10/1986 |
| GB | 1 508 460 | 4/1978 |
| GB | 2 147 896 | 5/1985 |
| WO | WO-97/35834 | 10/1997 |
| WO | WO-03/010125 | 2/2003 |
| WO | WO-2005/012223 | 2/2005 |

OTHER PUBLICATIONS

Kirk-Othmer Encyclopedia of Chemical Technology, 3rd Edition, vol. 7, pp. 580-602 1979.
Amines Alkyl, Abstract Process Economics Program Report, No. 138, Mar. 1981.
Kalbel et al., "Reaktionen in Destillationskolonnen", *Chem.-Ing.-Tech.*, vol. 50, No. 8, pp. 586-592 (1978).
Arne, Michael, "Alkyl Amines", from a private report by the Process Economics Program, SRI International, Menlo Park, CA, pp. 7-8, 13-16, 43-107, 113 and 117 (1981).

*Primary Examiner*—Brian J Davis
(74) *Attorney, Agent, or Firm*—Connolly Bove Lodge & Hutz, LLP

(57) ABSTRACT

Preparation of ethyleneamines by reacting monoethanolamine (MEOA) with ammonia in the presence of a catalyst in a reactor (1) and separating the resulting reaction product, where ethylenediamine (EDA) obtained in the separation is reacted in a separate reactor (2) in the presence of a catalyst to give diethylenetriamine (DETA), and the resulting reaction product is passed to the separation of the reaction product resulting from reactor 1.

14 Claims, 5 Drawing Sheets

Annex 1

5   Process sketch according to EP-A2-197 611

Annex 2

5   "Variant 1" of the process according to the invention

Annex 3

"Variant 2" of the process according to the invention

Annex 4

5   "Variant 3" of the process according to the invention (reactor 2 is a reaction column)

Annex 5

5    Reaction column for reacting EDA to give DETA

_US 7,601,875 B2_

METHOD FOR PRODUCING ETHYLENEAMINES

RELATED APPLICATIONS

This application is a national stage application (under 35 U.S.C. 371) of PCT/EP2004/007471 filed Jul. 8, 2004 which claims benefit to German application 103 35 991.5 filed Aug. 1, 2003.

The present invention relates to a process for the preparation of ethyleneamines by reacting monoethanolamine (MEOA) with ammonia in the presence of a catalyst in a reactor (1) and separating the resulting reaction product.

Ethyleneamines are used as solvents, stabilizers, for the synthesis of chelating agents, synthetic resins, medicaments, inhibitors and interface-active substances.

In particular, diethylenetriamine (bis(2-aminoethyl)amine; DETA) is used as a solvent for dyes and is a starting material for the preparation of ion exchangers, pesticides, antioxidants, corrosion inhibitors, complexing agents, textile auxiliaries and absorption agents for (acidic) gases.

The literature describes numerous processes for the preparation of ethyleneamines, including DETA.

According to PEP Report No. 138, "Alkyl Amines", SRI International, 03/1981, in particular pages 7, 8, 13-16, 43-107, 113, 117, the reaction of dichloroethane with ammonia at molar ratios of 1:15 produces diethylenetriamine (DETA) with a proportion of the formed ethyleneamines greater than 20% by weight. As well as 40% by weight of ethylenediamine (EDA), however, 40% by weight of higher ethyleneamines are produced.

By aminating monoethanolamine (MEOA) with ammonia (cf. e.g. the abovementioned PEP Report) it is possible to largely suppress the formation of these higher ethyleneamines (i.e. ethyleneamines with a boiling point above that of triethylenetetramine (TETA)) in favor of ethylenediamine. However, aminoethylethanolamine (AEEA) and piperazine (PIP) are produced as by-products in this reaction. Since the market demand for these two products is volatile relative to ethylenediamine and diethylenetriamine, a number of methods have been developed to increase the proportion of ethylenediamine and diethylenetriamine at the expense of aminoethylethanolamine and piperazine.

As a rule, this is achieved by reacting monoethanolamine only partially (40-60%) over transition metal catalysts (e.g. Ni, Co, Cu catalysts; U.S. Pat. No. 4,014,933 (BASF AG)) in the presence of hydrogen with a molar excess of ammonia ($NH_3$: MEOA>6).

By adding water (U.S. Pat. No. 3,766,184), varying the amount of hydrogen (U.S. Pat. No. 4,234,730 (Texaco)) and controlling the MEOA content (U.S. Pat. No. 4,647,701 (UCC)) it is possible to keep the content of piperazine plus aminoethylethanolamine of the formed ethyleneamines at MEOA conversions of 40-60% below 20% by weight. However, as a result of the high ammonia excess and the partial conversion of MEOA, the proportion of diethylenetriamine of the formed ethyleneamines is significantly below 20% by weight.

For the targeted preparation of diethylenetriamine, GB-A-2,147,896 (Mitsui Toatsu) describes the reaction of monoethanolamine with ethylenediamine and ammonia (EDA:MEOA:$NH_3$ in the molar ratio 2:1:18) in the presence of a phosphate-containing catalyst. At MEOA conversions of 65%, DETA selectivities of >90% are described. It is disadvantageous here that ammonia has to be used in excess and that high DETA selectivities are achieved only in the presence of EDA at partial MEOA conversion. Furthermore, a general problem of this technology is the low service life of the catalysts used under the drastic reaction conditions (280-350° C.).

To overcome this weakness, a large number of different phosphate-containing catalysts has been filed for patent (U.S. Pat. No. 4,683,335 (Texaco), U.S. Pat. No. 4,612,397 (Texaco), U.S. Pat. No. 4,609,761 (Texaco)). Apart from the gas-phase amination of hydroxyethylpiperazine to give triethylenediamine, these catalysts have hitherto been unable to penetrate the market.

Compared with the phosphate catalysis, ethylenediamine can be reacted with itself (GB-A 1,508,460 (BASF AG); U.S. Pat. No. 4,568,746 (UCC)) or with monoethanolamine (U.S. Pat. No. 3,714,259 (Jefferson Chemical); U.S. Pat. No. 4,568,746) over transition metal catalysts under a hydrogen atmosphere at considerably milder conditions (140-210° C.).

Under the conditions described in U.S. Pat. No. 3,714,259, about 0.45-0.84 kg of piperazine plus AEEA are formed per kg of DETA.

Higher DETA/piperazine ratios are achieved in U.S. Pat. No. 4,568,746 over Ni/Re catalysts (DETA/PIP=5.4-8.9 at 23-33% conversion) at temperatures of >17° C. and in GB-A-1,508,460 over Ni/Co/Cu catalysts (DETA/PIP=17-26 at 23% conversion) at temperatures of <150° C. and preferred pressures of from 25 to 45 bar.

U.S. Pat. No. 5,410,086 (Burgess) claims the control of the DETA/piperazine ratio by adjusting the hydrogen concentration in the liquid phase.

Disadvantages of these technologies (stand alone) are that no ethylenediamine is produced here and ammonia which is released as a result of the condensation of ethylenediamine is lost as feed material.

DD-A-213 206 relates to a process for the preparation of di- and polyethylenepolyamines by amination of monoethanolamine over a hydrogenation catalyst in a prereaction zone and a main reaction zone connected thereto.

DD-A-217 507 describes a process for the preparation of di- and polyethylenepolyamines by amination of monoethanolamine over a hydrogenation catalyst in two reaction steps, where the primary amination product from the first reaction step is reacted with a secondary amination product following removal of the excess ammonia.

EP-A2-197 611 (Union Carbide Corp.) describes a process in which the proportion of higher ethyleneamines of the formed ethyleneamines is increased through the use of two reactors connected in series.

The process is sketched in FIG. 1 (Annex 1). Cf. also FIG. 3 in EP-A-2 197 611.

In the first reactor, the amination of MEOA with ammonia takes place over transition metal catalysts (Ni, Re, support).

To increase the proportion of higher ethyleneamines, the reactor product is sent via a second reactor, which is likewise charged with a transition metal catalyst or with a phosphate catalyst.

To control the product distribution and to increase the selectivity with regard to the linear ethyleneamines, ethylenediamine which originates from the work-up of the reaction product from the second reactor and also comprises MEOA and $H_2O$ is introduced before the second reactor.

A disadvantage of this process is that AEEA further reacts preferentially to give piperazine and not to give DETA and additional amounts of AEEA are formed as a result of the reaction of EDA with MEOA.

A SUMMARY OF THE INVENTION

It is an object of the present invention to find an improved economical process for the preparation of ethyleneamines, where the ethyleneamines are, in particular, ethylenediamine (EDA), diethylenetriamine (DETA), aminoethylethanolamine (AEEA), piperazine (PIP) and/or triethylenetetramine (TETA), where the proportion of diethylenetriamine of the formed ethyleneamines is greater than 20% by weight, and the proportion of piperazine plus aminoethylethanolamine of the formed ethyleneamines can be limited, as required, to less than 15% by weight, at an overall yield with regard to EDA, DETA, AEEA and piperazine of greater than 90%.

We have found that this object is achieved by a process for the preparation of ethyleneamines by reacting monoethanolamine (MEOA) with ammonia in the presence of a catalyst in a reactor (1) and separating the resulting reaction product, which comprises reacting ethylenediamine (EDA) obtained in the separation in a separate reactor (2) in the presence of a catalyst to give diethylenetriamine (DETA), and passing the resulting reaction product to the separation of the reaction product resulting from reactor 1.

A DETAILED DESCRIPTION OF THE INVENTION

Figure 1:
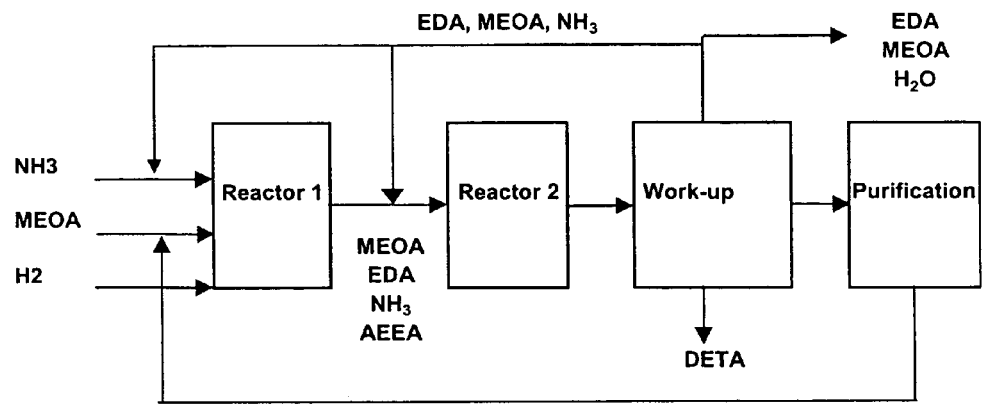
FIG. 1 illustrates a process sketch according to EP-A2-197 611.

The process can be carried out as follows.

The reaction of monoethanolamine with ammonia in reactor 1, which may of course also be divided into two or more reactors connected in series or in parallel, can be carried out by processes known to the person skilled in the art (see e.g. PEP Report No. 138, "Alkyl Amines", SRI International, 03/1981, pages 81-99, 117, and literature cited at the outset).

The reaction of monoethanolamine with ammonia is carried out in reactor (1) preferably over a transition metal catalyst at generally 150-250 bar and generally 160-210° C. and over a zeolite catalyst at generally 1-20 bar and generally 280-380° C.

Reactor 1 is preferably a fixed-bed reactor.

Preferably used transition metals in the catalyst are Ni, Co, Cu, Ru, Re, Rh, Pd or Pt or a mixture of two or more of these metals on an oxidic support (e.g. $Al_2O_3$, $TiO_2$, $ZrO_2$, $SiO_2$).

Preferred zeolite catalysts are mordenites, faujasites and chabazites.

To achieve the highest possible selectivity with regard to the linear amines EDA and DETA, the molar ratio of ammonia to monoethanolamine in the case of the transition metal catalysis is generally 6-20, preferably 8-15, and in the case of zeolite catalysis generally 20-80, preferably 30-50.

The MEOA conversion is generally kept in the range between 10% and 80%, preferably 40-60%.

Under the stated reaction conditions, in the preferably continuous operation at a WHSV (weight hourly space velocity) in the range from 0.3-0.6 kg/(kg*h) (kg of MEOA per kg of catalyst per hour), a selectivity for EDA+DETA with regard to reacted MEOA of preferably >80%, in particular 83-85%, is achieved.

To maintain the catalyst activity, in the case of the use of metal catalysts, 0.05-0.5% by weight (based on the reactor feed M-OA+$NH_3$+$H_2$) of hydrogen are preferably additionally introduced into reactor 1.

The reactor product is then decompressed to preferably 20-30 bar. The "low-pressure hydrogen" produced during this can be used directly or following removal of ammonia via a gas scrubbing as feed for reactor 2 (see below).

The reaction product which remains following removal of the hydrogen and comprises essentially or consists of ammonia, water, ethylenediamine, piperazine, monoethanolamine, diethylenetriamine, aminoethylethanolamine, triethylenetetramine (TETA) and higher ethyleneamines (i.e. ethyleneamines with a higher boiling point than TETA (at the same pressure), is separated into the individual constituents according to the vapor pressures.

The multistage separation into the constituents preferably takes place by distillation, in particular by continuous distillation. Such separation processes are known to the person skilled in the art, for example, from the abovementioned PEP Report No. 138.

The distillation columns required for distillative purification of the individual products, primarily of the desired ethyleneamines, can be designed by the person skilled in the art using methods with which he is familiar (e.g. number of plates, reflux ratio, etc.).

The separation of the reaction product resulting from reactor 1 is particularly preferably in two separation sequences by multistage distillation, where in the first separation sequence (separation sequence 1) firstly ammonia, water and if appropriate hydrogen present are separated off, and in the second separation sequence (separation sequence 2), a separation into EDA, PIP, MEOA, DETA, AEP, HEP, AEEA, TETA and higher ethyleneamines takes place. (AEP=N-(2-aminoethyl) piperazine; HEP=N-(2-hydroxyethyl)piperazine).

During this separation of the reaction product resulting from reactor 1, if appropriate monoethanolamine produced as a result of incomplete reaction is preferably returned to reactor 1.

The ethylenediamine (EDA) produced during this separation is, if appropriate after diverting a partial amount, as required, to a storage tank, passed to a separate reactor (2) for the reaction to diethylenetriamine (DETA) in the presence of a catalyst.

The reaction of EDA to DETA in reactor 2, which of course can also be divided into two or more reactors connected in series or in parallel, can be carried out by processes known to the person skilled in the art (see e.g. U.S. Pat. No. 5,410,086 (Burgess) and GB-A-1,508,460 (BASF AG) and WO-A1-03/ 010125 (Akzo Nobel)).

The reaction of ethylenediamine to diethylenetriamine preferably takes place over a transition metal catalyst. The metals preferably used here are Ni, Co, Cu, Ru, Re, Rh, Pd or Pt or a mixture of two or more of these metals on an oxidic support (e.g. $Al_2O_3$, $TiO_2$, $ZrO_2$, $SiO_2$).

As an alternative to the transition metal catalysts, it is also possible to use shape-selective zeolite catalysts or phosphate catalysts for this reaction.

The reaction over transition metal catalysts generally takes place at a pressure of 1-200 bar, preferably at 1-30 bar, and generally in the temperature range from 130-170° C., preferably at 140-160° C.

In one embodiment, the reactor 2 can also be operated with a mixture of MEOA and EDA, where EDA is used in molar excess, e.g. in the molar EDA:MEOA ratio of >5. However, preference is given to using only EDA since here, compared with EP-A2-197 611, the formation of additional amounts of AEEA in reactor 2 can be suppressed completely.

To maintain the catalyst activity, 0.01-0.15% by weight of hydrogen (based on the EDA+$H_2$ reactor feed) are preferably introduced into the reactor.

In the preferably continuous operation at a WHSV of 0.5-1.5 kg/kg*h (kg of EDA per kg of catalyst per hour) in the conversion range of 15-30%, selectivities (S) with regard to DETA of preferably ≧75%, in particular 75-85%, are achieved.

During this reaction, small amounts of piperazine ($S_{PIP}$ generally 8-13%) and triethylenetetramine ($S_{TETA}$ generally 5-10%) are produced as by-products.

The ammonia- and if appropriate optionally hydrogen-containing reaction product of the separate reaction of EDA to DETA is combined, in one embodiment of the process according to the invention (variant 1), with the product from reactor 1 and worked-up together, i.e. is passed to the separation of the reaction product resulting from reactor 1, in particular the first separation sequence (separation sequence 1) of the separation of the reaction product resulting from reactor 1.

Figure 2:
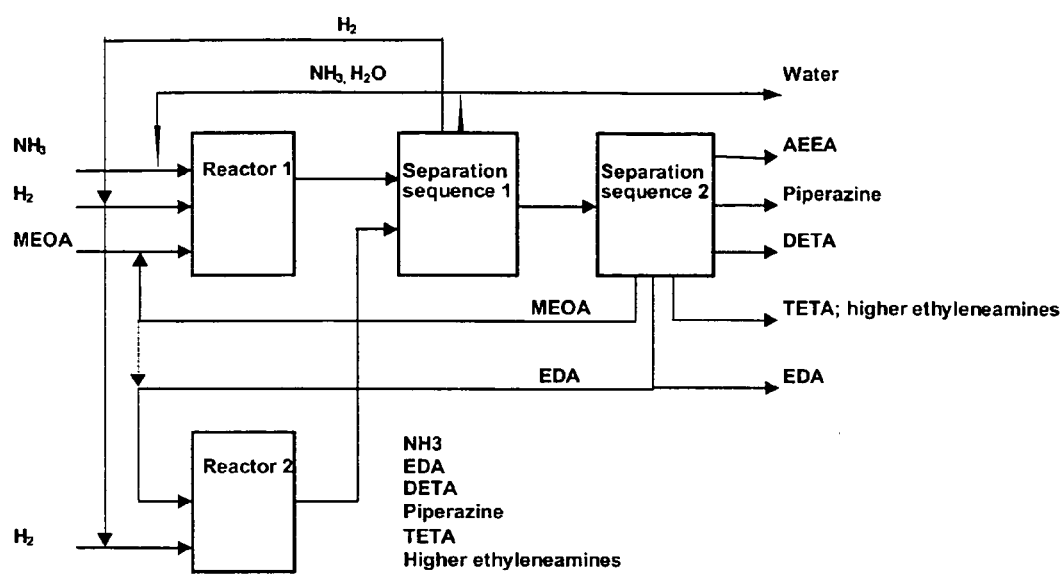
FIG. 2 illustrates a process scheme according to the invention.

A process scheme of this variant 1 of the process according to the invention is given in Annex 2 (FIG. 2).

In a further embodiment of the process according to the invention (variant 2), ammonia and optionally hydrogen are firstly separated off from the reaction product of the separate reaction of EDA to DETA (separation sequence 3), and the reaction product which remains, comprising ethyleneamines, is then passed to the second separation sequence (separation sequence 2) of the separation of the reaction product resulting from reactor 1.

Figure 3:
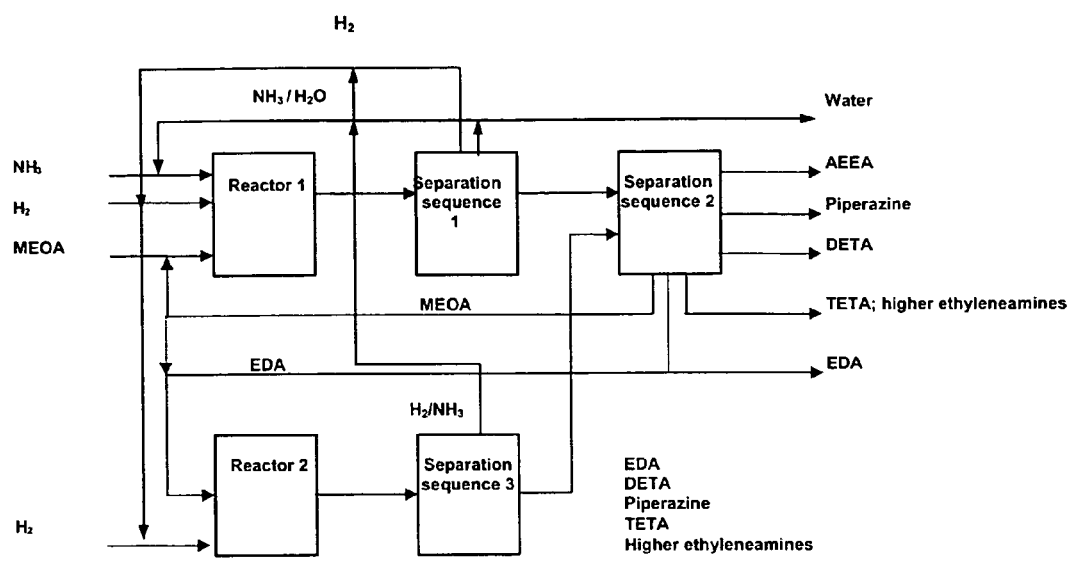
FIG. 3 illustrates another process scheme according to the invention.

A process scheme of this variant 2 of the process according to the invention is given in Annex 3 (FIG. 3).

In a further particular embodiment of the process according to the invention (variant 3, which represents a particular version of variant 2), the reaction of ethylenediamine to diethylenetriamine is carried out with the elimination of ammonia in a reaction column, preferably continuously (reactive distillation).

Unreacted ethylenediamine is returned via the reflux of the reaction column, ammonia and optionally hydrogen are removed overhead and in each case optionally returned to the process (to reactor 1).

An advantage of this variant is the continuous removal of ammonia from the condensation equilibrium. The reaction temperature is adjusted here via the column pressure.

Figure 4:
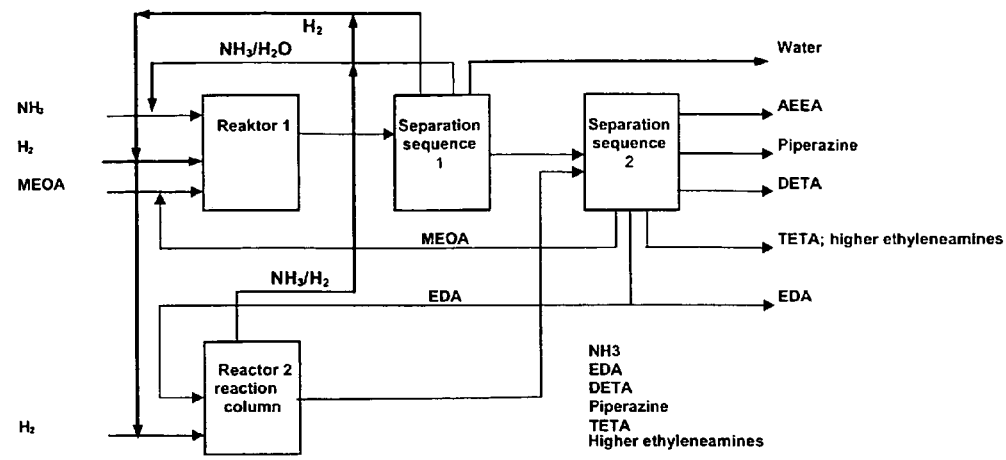
FIG. 4 illustrates another process scheme according to the invention.
Figure 5:
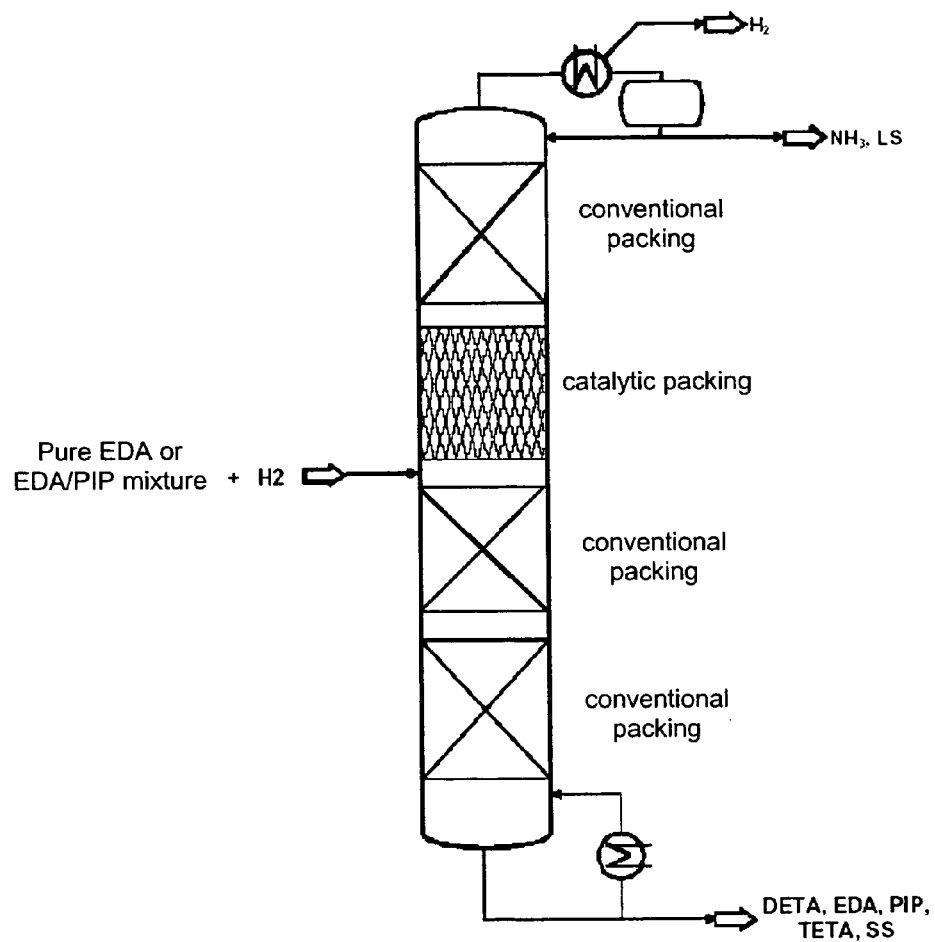
FIG. 5 illustrates a reaction column for reacting EDA to give DETA.

A process diagram of this variant 3 of the process according to the invention is given in Annex 4 (FIG. 4).

The design of the reaction column (e.g. number of plates in the column sections, enriching section, stripping section and reaction zone, reflux ratio, etc.) can be undertaken by the person skilled in the art in accordance with methods with which he is familiar.

Reaction columns are known to the person skilled in the art, for example from G. Kaibel et al., Chem.-lng.-Tech. 50 (1978), No. 8, pages 586-592, and the literature cited therein and WO-A1-97/35834.

The processes also referred to as reactive distillation are described in detail, for example, also in the textbook "Reactive Distillation", edited by K. Sundmacher and A. Kienle, Verlag Wiley-VCH (2003).

The continuous reaction of ethylenediamine to ethyleneamines, in particular to diethylenetriamine, with the elimination of ammonia in a reaction column in the presence of a heterogeneous catalyst is the subject-matter of a parallel German patent application from BASF AG with the same filing date.

An exemplary process scheme for a reaction column which can be used is given in Annex 5. According to this, pure EDA or an EDA/PIP mixture is passed together with hydrogen to the reaction column continuously below the catalytic packing, and a mixture comprising DETA, unreacted EDA, PIP, TETA and high-boiling components (SS, i.e. components with a boiling point greater than that of DETA) is obtained via the bottom. Ammonia, hydrogen and low-boiling components (LS, i.e. components with a boiling point lower than that of DETA) are separated off overhead.

The absolute pressure in the reaction column for the reaction of EDA to DETA is generally adjusted to 1-20 bar, preferably to 5-10 bar, and the temperature in the catalytically active zone (reaction zone) is generally adjusted to 100-200° C., preferably to 140-160° C.

The catalytically active zone used in the reaction column is a heterogeneous catalyst preferably either poured loose into a conventional distillation packing, or a packing material with a catalytically active surface (thin-layer catalysis).

The catalytically active material which may be used is either transition metals (e.g. Ni, Co, Cu, Ru, Re, Rh, Pd and/or Pt) and also zeolithic coatings or phosphate catalysts. The metal or the metals of the transition metal catalyst are preferably applied to an oxidic support (e.g. $Al_2O_3$, $TiO_2$, $ZrO_2$, $SiO_2$).

The catalytically active zone consists of generally 5-30, preferably 10-20, theoretical plates above the column feed, and the distillative zones each consist of generally 5-30, preferably 10-20, theoretical plates above and below the catalytically active packing.

The column reflux: feed-weight ratio is generally 0.5-10, preferably 0.5-2.

To maintain the catalyst activity, preferably hydrogen is introduced, preferably below the catalytic packing. The preferred amount here is 0.01 to 1% by weight of hydrogen, based on the feed amount of EDA.

Liberated ammonia and if appropriate hydrogen is separated off overhead, and the reaction products DETA, piperazine and higher ethyleneamines together with unreacted ethylenediamine via the bottom.

The EDA conversion may be adjusted here via the bottom temperature.

It is a characteristic of the process according to the invention that by integrating the condensation stage EDA→DETA (reactor 2) into a conventional ethyleneamine process based on monoethanolamine, the two reactor products can be worked-up together.

Liberated ammonia which is produced during work-up can be returned to the amination of MEOA (reactor 1), and offgas hydrogen, which is produced if appropriate in the amination of MEOA, can be used as feed for the condensation reactor (reactor 2).

It has been found that the mixing of the two products from reactor 1 and 2 prior to work-up and the abovementioned possible utilization of ammonia and offgas hydrogen have no negative effect on the product quality of the ethyleneamines, in particular of EDA and DETA.

Compared to the direct further processing of the reaction product from reactor 1 according to EP-A2-197 611, the selective conversion of EDA in reactor 2 achieves considerably higher selectivities with regard to linear ethyleneamines (EDA+DETA).

EXAMPLES

Example 1

A mixture of monoethanolamine, ammonia and hydrogen (molar ratio of MEOA:$NH_3$:$H_2$=1:8:0.14) was passed at a WHSV of 0.4 kg/kg/h (kg of MEOA per kg of catalyst per hour) at a temperature of 170° C. and a pressure of 200 bar continuously into a tubular reactor (reactor 1) which was charged with a catalyst, consisting of 4% by weight of copper, 6% by weight of cobalt and 8% by weight of nickel (in each case based on the supported catalyst) on an aluminum oxide support. The product obtained was a mixture consisting of 65.7% by weight of ammonia, 4.4% by weight of water, 15.5% by weight of MEOA, 10.9% by weight of EDA, 1.3% by weight of DETA, 0.9% by weight of AEEA, 0.74% by weight of piperazine and 0.56% by weight of TETA, AEP, HEP+higher ethyleneamines. (Higher ethyleneamines=ethyleneamines with a boiling point higher than that of TETA (at the same pressure)).

A mixture of ethylenediamine and hydrogen (molar ratio 50:1) was passed at a WHSV of 0.7 kg/kg/h (kg of EDA per kg of catalyst per hour) into a second reactor (reactor 2), which was likewise charged with a catalyst consisting of 4% by weight of copper, 6% by weight of cobalt and 8% by weight of nickel (in each case based on the supported catalyst) on an aluminum oxide support. The reaction pressure was adjusted here to 30 bar and the reaction temperature to 150° C. The product obtained was a mixture consisting of 5.1% by weight of ammonia, 69.9% by weight of ethylenediamine, 19.3% by weight of diethylenetriamine, 2.6% by weight of piperazine and 3.1% by weight of TETA, AEP, HEP+higher ethyleneamines.

The products of the two reactors are combined and separated into the individual components by means of multistage continuous distillation. At 80% recycle of ethylenediamine that is produced in reactor 2, a product mixture consisting of 28% by weight of ethylenediamine, 24% by weight of water, 28% by weight of diethylenetriamine, 8% by weight of piperazine, 6% by weight of aminoethylethanolamine and 6% by weight of TETA, AEP, HEP+higher ethyleneamines is obtained.

Prior to separating off the ammonia, low-pressure hydrogen which has formed is passed to reactor 2 to maintain the catalyst activity.

Liberated ammonia from the condensation of ethylenediamine to diethylenetriamine is returned to the amination of monoethanolamine (in reactor 1).

Example 2

A mixture of monoethanolamine, ammonia and hydrogen (molar ratio MEOA:$NH_3$:$H_2$=1:10:0.14) was passed at a WHSV of 0.4 kg/kg/h (kg of MEOA per kg of catalyst per hour) at a temperature of 170° C. and a pressure of 200 bar continuously into a tubular reactor which was charged with a Cu/Co/Ni catalyst, as in Example 1. The product obtained was a mixture consisting of 70.7% by weight of ammonia, 3.7% by weight of water, 13.2% by weight of MEOA, 9.5% by weight of EDA, 1.1% by weight of DETA, 0.68% by weight of AEEA, 0.56% by weight of piperazine and 0.56% by weight of TETA, AEP, HEP+higher ethyleneamines.

A mixture of ethylenediamine and hydrogen (molar ratio 50:1) was passed at a WHSV of 1.1 kg/kg/h (kg of EDA per kg of catalyst per hour) into a second reactor (reactor 2), which was likewise charged with a Cu/Co/Ni catalyst, as in Example 1. The reaction pressure was adjusted here to 30 bar and the reactor temperature to 160° C. The product obtained was a mixture consisting of 4.2% by weight of ammonia, 75.0% by weight of ethylenediamine, 16.7% by weight of diethylenetriamine, 2.6% by weight of piperazine and 1.5% by weight of TETA, AEP, HEP+higher ethyleneamines.

The products of the two reactors are combined and separated into the individual components by means of continuous distillation. At 60% recycle of ethylenediamine that is produced in reactor 2, a product mixture consisting of 37% by weight of ethylenediamine, 24% by weight of water, 23.4% by weight of diethylenetriamine, 6% by weight of piperazine, 4.4% by weight of aminoethylethanolamine and 5.2% by weight of TETA, AEP, HEP+higher ethyleneamines is obtained.

Prior to separating off the ammonia, low-pressure hydrogen which has formed is passed to reactor 2 to maintain the catalyst activity.

Liberated ammonia from the condensation of ethylenediamine to diethylenetriamine is returned to the amination of monoethanolamine (in reactor 1).

We claim:

1. A process for the preparation of ethyleneamines by reacting monoethanolamine (MEOA) with ammonia in the presence of a catalyst in a reactor (1) and separating the resulting reaction product, which comprises reacting ethylenediamine (EDA) obtained during the separation in a separate reactor (2) in the presence of a catalyst to give diethylenetriamine (DETA), and the resulting reaction product is passed to the separation of the reaction product resulting from reactor 1.

2. The process for the preparation of ethyleneamines according to claim 1, where the ethyleneamines are EDA, DETA, aminoethylethanolamine (AEEA), piperazine (PIP) and/or triethylenetetramine (TETA).

3. The process for the preparation of ethyleneamines according to claim 1, where the proportion of DETA is greater than 20% by weight.

4. The process according to claim 1, wherein the reaction in reactor 1 is carried out in the presence of a transition metal catalyst or a zeolite.

5. The process according to claim 4 wherein the transition-metal catalyzed reaction in reactor 1 is carried out in the presence of hydrogen.

6. The process according to claim 1, wherein the separation of the reaction product resulting from reactor 1 takes place by multistage distillation.

7. The process according to claim 2, wherein the separation of the reaction product resulting from reactor 1 takes place in two separation sequences (a first separation sequence and a second separation sequence by multistage distillation, where in the first separation sequence firstly ammonia, water and optionally hydrogen present are separated off, and in the second separation sequence a separation in to EDA, PIP, MEOA, DETA, N-(2-aminoethyl)piperazine (AEP), N-(2-hydroxyethyl)piperazine (HEP), AEEA, TETA and higher ethyleneamines takes place.

8. The process according to claim 1, wherein the reaction in reactor 2 is carried out in the presence of a transition metal catalyst, a zeolite or a phosphate catalyst.

9. The process according to claim 8, wherein the transition-metal catalyzed reaction in reactor 2 is carried out in the presence of hydrogen.

10. The process according to claim 7, wherein the reaction product resulting from reactor 2, comprising ammonia and DETA, is passed to the first separation sequence of the separation of the reaction product resulting from reactor 1.

11. The process according to claim 7, wherein ammonia and optionally hydrogen is separated off from the reaction product resulting from reactor 2 (separation sequence 3) and the reaction product is then passed to the second separation sequence of the separation of the reaction product resulting from reactor 1.

12. The process according to claim 11, wherein the reaction of the EDA to give DETA and the removal of the ammonia is carried out in a reaction column.

13. The process according to claim 1, wherein ammonia that is produced during the separation of the reaction product resulting from reactor 1 is returned to reactor 1.

14. The process according to claim 11, wherein the ammonia separated off from the resulting reaction product of reactor 2 or the ammonia separated off from the reaction column is returned to reactor 1.

* * * * *

UNITED STATES PATENT AND TRADEMARK OFFICE
CERTIFICATE OF CORRECTION

PATENT NO. : 7,601,875 B2
APPLICATION NO. : 10/566694
DATED : October 13, 2009
INVENTOR(S) : Matthias Frauenkron et al.

It is certified that error appears in the above-identified patent and that said Letters Patent is hereby corrected as shown below:

On the Title Page

Item (75): Inventors: "Till Gerlack" should read -- Till Gerlach --

Item (56): References Cited: Other Publications, document listed as "Kalbel et al., "Reaktionen in Destillationskolonnen", *Chem.-Ing.-Tech.*, vol. 50, No. 8, pp. 586-592 (1978)." should read -- Kaibel *et al.*, "Reaktionen in Destillationskolonnen", *Chem.-Ing.-Tech.*, Vol. 50, No. 8, pp. 586-592 (1978). --

In Claim 7, at column 8, lines 57-58, "two separation sequences (a first separation sequence and a second separation sequence by multistage distillation, where" should read -- two separation sequences (a first separation sequence and a second separation sequence) by multistage distillation, where --

Signed and Sealed this

Twenty-second Day of December, 2009

David J. Kappos
*Director of the United States Patent and Trademark Office*

UNITED STATES PATENT AND TRADEMARK OFFICE
CERTIFICATE OF CORRECTION

PATENT NO.       : 7,601,875 B2                                  Page 1 of 1
APPLICATION NO.  : 10/566694
DATED            : October 13, 2009
INVENTOR(S)      : Frauenkron et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 770 days.

Signed and Sealed this

Fifth Day of October, 2010

David J. Kappos
*Director of the United States Patent and Trademark Office*